United States Patent [19]

Chen et al.

[11] Patent Number: 6,140,515
[45] Date of Patent: *Oct. 31, 2000

[54] PROCESS OF MAKING 3-ARYLOXY, 4-ARYL FURAN-2-ONES USEFUL AS INHIBITORS OF COX-2

[75] Inventors: Cheng Y. Chen, Colonia; Lushi Tan, Edison; Robert D. Larsen, Bridgewater, all of N.J.

[73] Assignee: Merck & Co., Inc., Rahway, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 09/153,403

[22] Filed: Sep. 15, 1998

Related U.S. Application Data

[60] Provisional application No. 60/060,694, Sep. 24, 1997.

[51] Int. Cl.[7] ............... C07D 307/12; C07D 307/26; C07D 401/12; C07D 405/12; C07C 315/00

[52] U.S. Cl. ............... 549/324; 546/256; 546/283.4; 568/28; 568/56

[58] Field of Search ................................. 549/324

[56] References Cited

U.S. PATENT DOCUMENTS

| | | | |
|---|---|---|---|
| 5,393,790 | 2/1995 | Reitz et al. ............ | 514/709 |
| 5,789,413 | 8/1998 | Black et al. ............ | 514/255 |

OTHER PUBLICATIONS

Chemical Abstracts, vol. 127, No. 1, Abst. No. 127:50026, Jul. 7, 1997.

Chemical Abstracts, vol. 127, No. 3, Abst. No. 127:34,1120, Jul. 21, 1997.

*Primary Examiner*—Alan L. Rotman
*Attorney, Agent, or Firm*—Richard C. Billups; David L. Rose

[57] ABSTRACT

Described is a process of preparing 3-aryl, 4-aryloxy furan-5-ones which are useful as inhibitors of cyclooxygenase-2 (COX-2). Such compounds are useful as anti-inflammatory agents. The process is directed to an asymmetric synthesis which involves: a trisubstituted styrene derivative preparation via Horner-Wadsworth-Emmons reaction and subsequent one pot trifluoromethylation of the allylic alcohol; preparation of the α-hydroxyl ketone using Sharpless asymmetric dihydroxylation and Swern oxidation; the esterification of the α-hydroxyl ketone with the phenoxy acetic acid; and the Dieckman condensation of the resulting ester.

14 Claims, No Drawings

PROCESS OF MAKING 3-ARYLOXY, 4-ARYL FURAN-2-ONES USEFUL AS INHIBITORS OF COX-2

CROSS REFERENCE TO RELATED APPLICATIONS

This application is a non-provisional based upon provisional application Ser. No. 60/060,694, filed on Sep. 24, 1997 priority of which is claimed hereunder.

BACKGROUND OF THE INVENTION

The invention described is a process of preparing 3-aryloxy, 4-aryl furan-2-ones which are useful as inhibitors of cyclooxygenase-2 (COX-2). Such compounds are useful as anti-inflammatory agents.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 (COX-1) or the constitutive enzyme, as originally identified in bovine seminal vesicles. More recently the gene for a second inducible form of cyclooxygenase, cyclooxygenase-2 (COX-2) has been cloned, sequenced and characterized initially from chicken, murine and human sources. This enzyme is distinct from the COX-1 which has been cloned, sequenced and characterized from various sources including the sheep, the mouse and man. The second form of cyclooxygenase, COX-2, is rapidly and readily inducible by a number of agents including mitogens, endotoxin, hormones, cytokines and growth factors. As prostaglandins have both physiological and pathological roles, we have concluded that the constitutive enzyme, COX-1, is responsible, in large part, for endogenous basal release of prostaglandins and hence is important in their physiological functions such as the maintenance of gastrointestinal integrity and renal blood flow. In contrast, we have concluded that the inducible form, COX-2, is mainly responsible for the pathological effects of prostaglandins where rapid induction of the enzyme would occur in response to such agents as inflammatory agents, hormones, growth factors, and cytokines. Thus, a selective inhibitor of COX-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

Furthermore, such a compound will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis) and for the treatment of glaucoma.

A brief description of the potential utility of cyclooxygenase-2 inhibitors is given in an article by John Vane, *Nature*, Vol. 367, pp. 215–216, 1994, and in an article in *Drug News and Perspectives*, Vol. 7, pp. 501–512, 1994.

The instant Compounds, their use and alternative methods of making the compounds are disclosed in PCT application CA 96/00682, filed Sep. 10, 1996, which hereby incorporated by reference.

SUMMARY OF THE INVENTION

Described is a process of preparing 3-aryloxy, 4-aryl furan-2-ones which are useful as inhibitors of cyclooxygenase-2 (COX-2). Such compounds are useful as anti-inflammatory agents. The process is directed to an asymmetric synthesis which involves: a trisubstituted styrene derivative preparation via Hoerner-Wadsworth-Emmons reaction and subsequent one pot trifluoromethylation of the allylic alcohol; preparation of the α-hydroxyl ketone using Sharpless asymmetric dihydroxylation and Swern oxidation; the esterification of the α-hydroxyl ketone with the phenoxy acetic acid; and the Dieckman condensation of the resulting ester.

DETAILED DESCRIPTION OF THE INVENTION

In one aspect the invention encompasses a method of making compounds of Formula I

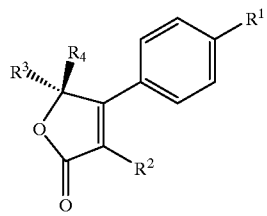

I or a pharmaceutical salt thereof wherein $R^1$ is selected from the group consisting of $SCH_3$, $-S(O)_2CH_3$ and $-S(O)_2NH_2$;

$R^2$ is selected from the group consisting of OR, mono or di-substituted phenyl or pyridyl wherein the substituents are selected from the group consisting of methyl, chloro and F;

R is unsubstituted or mono or di-substituted phenyl or pyridyl wherein the substituents are selected from the group consisting of methyl, chloro and F;

$R^3$ is H, $C_{1-4}$alkyl optionally substituted with 1 to 3 groups of F, Cl or Br and $R^4$ is H, $C_{1-4}$alkyl optionally substituted with 1 to 3 groups of F, Cl or Br, with the proviso that $R^3$ and $R^4$ are not the same.

The process as disclosed herein is of particular advantage in the preparation of 5,5-dialkyl or optionally such compounds as compound 12 3-(3,4-difluorophenoxy)-4-(4-methylsulfonylphenyl)-5-methyl-5-trifluoroethyl-(5H)-furan-2-one:

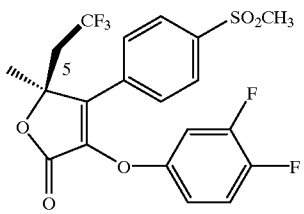

12

The quaternary substituted chiral center at C(5) considerably increases the difficulty of its synthesis. In this application the applicants describe a highly efficient asymmetric synthesis (as Exemplified by the synthesis of compound 12, hereunder) along with the discovery of a one pot transformation of allylic alcohols to trifluoromethylated compounds.

Preparation of the (E)-allylic alcohols 4a and 4b is illustrated in Scheme 1. Hoerner-Wadsworth-Emmons reaction of aldehyde 5 with triethyl 2-phosphonopropionate under known conditions afforded the α, β-unsaturated ester 6a. Oxidation of 6a with $H_2O_2$ in methanol in the presence of catalytic amount of $Na_2WO_4$, after diluted with water, produced the crystalline 6b. Both 6a and 6b were reduced with DIBAL-H in dichloromethane to give the corresponding alcohols 4a and 4b.

Scheme 1

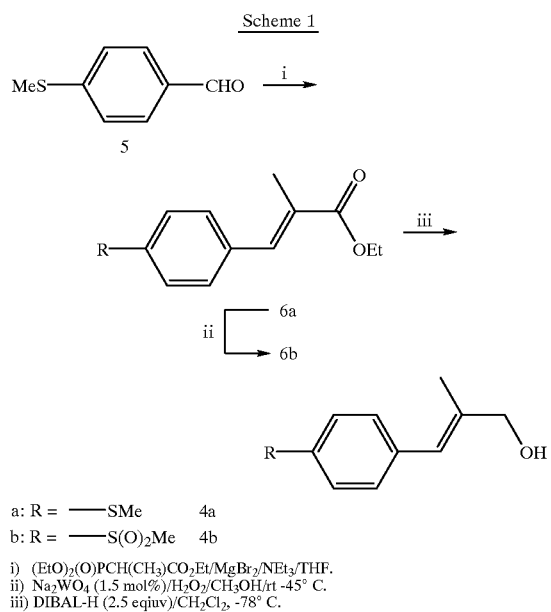

a: R = ——SMe    4a
b: R = ——S(O)$_2$Me    4b i) (EtO)$_2$(O)PCH(CH$_3$)CO$_2$Et/MgBr$_2$/NEt$_3$/THF.
ii) Na$_2$WO$_4$ (1.5 mol%)/H$_2$O$_2$/CH$_3$OH/rt -45° C.
iii) DIBAL-H (2.5 eqiuv)/CH$_2$Cl$_2$, -78° C.

In the effort to convert allylic alcohol 4b into the corresponding trifluoromethylated compound 3b, applicants first developed a modification of the process developed by Duan and co-workers (Scheme 2). See Duan, J. -X., et al J. Fluorine Chem. 1993, 61, pg 279. Conversion of 4b to 7 was facilitated by treating 4b with iodine in the presence of triphenyphosphine and imidazole in acetonitrile at 0° C. The allylic iodide 7 was isolated after flash chromatography. Unfortunately, the coupling reaction of 7 with an alkyl cuprate such as trifluoromethylcuprate at 110–120° C. to afford the styrene derivative 3b was inefficient. The required chromatography for the isolation of both 7 and 3b make the procedure not as useful.

Scheme 2

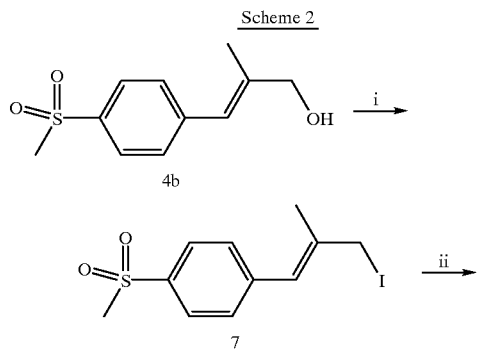

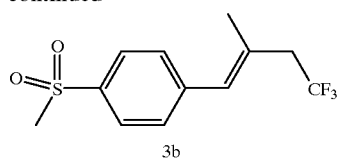

i) I$_2$/PPh$_3$/ImH/acetonitrile.
ii) ClCF$_2$CO$_2$Me/KF/CuI/DMF/90° C.

Detailed study of the trifluoromethylation reaction revealed that ester 8b was one of the intermediates. Alternatively, intermediate 8b was generated in DMF by treating allylic alcohol 4b with chlorodifluoroacetic anhydride. Heating the solution with 1.1 equiv of KF and 1 equiv of CuI at 90° C. for 1 h cleanly produced the desired product 3b. In our optimized conditions 3b was efficiently isolated. Similarly, 4a was converted to 3a. The choice of base is very important for the reaction. Hindered bases such as diisopropylethylamine gave the best result. In addition, the reaction was observed when as little as approximately one equiv of CuI was used. This process constitutes a virtually one step preparation of trifluoromethylated compounds from allylic alcohols.

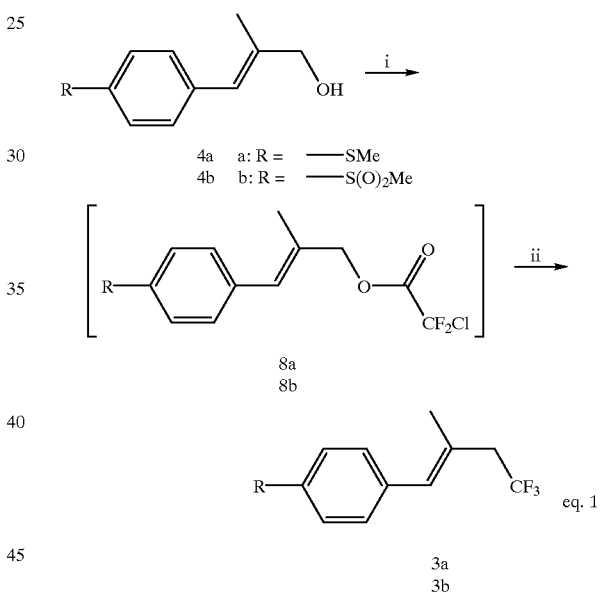

4a  a: R = ——SMe
4b  b: R = ——S(O)$_2$Me 8a
8b 3a
3b
eq. 1 i) (CF$_2$ClCO)$_2$O/DMF/base.
ii) KF, CuI, 90° C.

The asymmetric dihydroxylation reaction of 3b with commercially available AD-mix-β and the procedure described by Sharpless afforded diol 9b. After extensive study in the optimization of the reaction conditions to improve the enantioselectivity we found that the reaction was best carried out under the conditions shown in eq. 2 with (DHQD)$_2$PHAL as ligand. The reaction went to completion in 5–6 h to give 9b. Since the chiral ligand plays a crucial role in the asymmetric dihydroxylation reactions applicants also explored whether change in ligand would help in our reaction. The best ligand by far, as shown in Table 1, was (DHQD)$_2$PHAL. Under the same reaction conditions the asymmetric dihydroxylation of 3a gave a mixture of 9a, 9b, and 9c in a ratio of 74:10:6 after 22 h. The mixture, after a simple extraction and solvent switch, was converted to 9b by treating it with $H_2O_2$ in methanol in the presence of catalytic amount of Na$_2$WO$_4$. Diol 9b was upgraded to >98% ee by a single recrystallization from a mixture of isopropyl acetate and hexane.

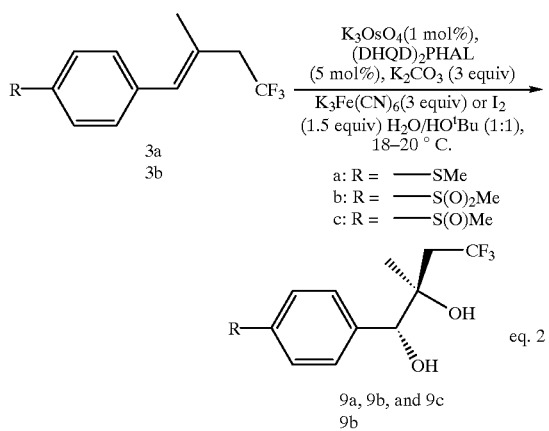

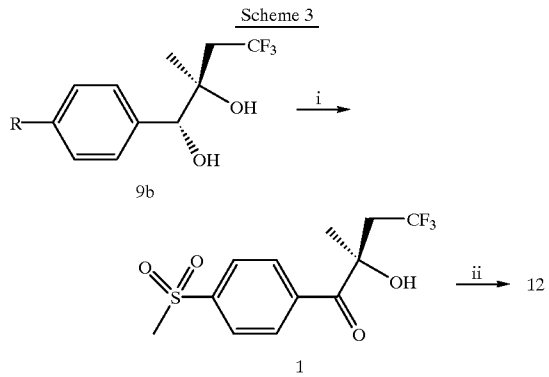

Scheme 3 i) DMSO (4.2 equiv)/ClCOCOCl (2.1 equiv)/CH2Cl2/-78° C., 30 min then NEt3 (9 equiv)/-78° C. to rt.
ii) 2/CMC/CH2Cl2/DMAP (10 mol%) 4 h then BU(1.2equiv)/ CF3CO2CH(CH3)2 (1.2 equiv)

TABLE 1

Asymmetric Dihydroxylation of Olefin 3b

| Entry | Ligand | Product 9b (% ee) |
|---|---|---|
| 1 | (DHQD)$_2$PHAL | 79 |
| 2 | (DHQD)$_2$-DP-PHAL | 70 |
| 3 | (DHQD)$_2$PYR | 69 |
| 4 | (DHQD)-PHN | 67 |
| 5 | (DHQD)$_2$AQN | 64 |
| 6 | (DHQD)$_2$DPP | 61 |
| 7 | (DHQD)-CLB | 41 |

The α-hydroxy keton 1 was formed in optimal yield through the Swern oxidation of 9b provided that at least 4 equiv of oxidizing reagents were used. The product was crystallized from toluene to afford analytically pure 1. Conversion of 1 and 3,4-difluorophenoxylacetic acid 2 to 12 was accomplished in one pot via an esterification using 1-cyclohexyl-3-(2-morpholino-ethyl)carbodiimide metho-p-toluenesulfonate (CMC) and catalytic amount of DMAP and the subsequent Dieckman condensation initiated by DBU (Scheme 3). It was found that complete conversion was observed only when isopropyl trifluoroacetate (1.2 equiv) was used as a water scavenger. The product was purified by recrystallization in ethanol to afford optically pure 12 from 1.

Thus, we have developed a practical synthesis of COX-2 inhibitor 12 with an improved overall yield. No chromatography was required in the process. The one step transformation of allylic alcohols to trifluoromethylated compounds provides an efficient an enhanced method for introducing the trifluoromethyl group.

Accordingly, the invention encompasses a process of making compounds of formula I

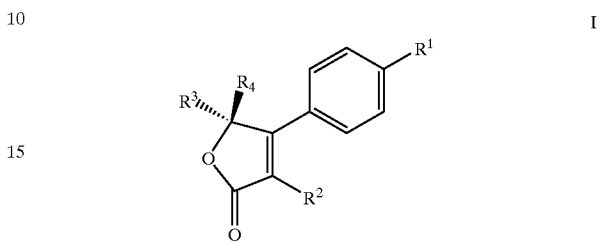

or a pharmaceutical salt thereof wherein $R^1$ is selected from the group consisting of $SCH_3$, $—S(O)_2CH_3$ and $—S(O)_2NH_2$;

$R^2$ is selected from the group consisting of OR, mono or di-substituted phenyl or pyridyl wherein the substituents are selected from the group consisting of methyl, chloro and F;

R is unsubstituted, mono or di-substituted phenyl or pyridyl wherein the substituents are selected from the group consisting of methyl, chloro and F;

$R^3$ is H, $C_{1-4}$alkyl optionally substituted with 1 to 3 groups of F, Cl or Br and $R^4$ is H, $C_{1-4}$alkyl optionally substituted with 1 to 3 groups of F, Cl or Br, with the proviso that $R^3$ and $R^4$ are not the same, the process comprising the steps of (a) reacting a compound of formula 3

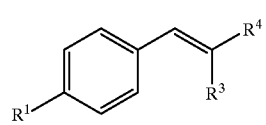

wherein $R^1$, $R^3$ and $R^4$ are described above;
with a first ligand, a basic buffer, an oxidant, and optionally a co-oxidant to yield a compound of formula 9

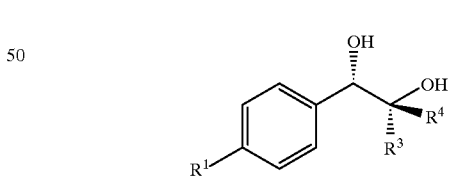

For purposes of this specification, the first ligand shall include, (DHQD)$_2$PHAL, (DHQD)$_2$DP-PHAL, (DHQD)$_2$PYR, (DHQD)-PHN, (DHQD)$_2$AQN, (DHQD)$_2$DPP and (DHQD)-CLB, preferably (HDQD)$_2$PHAL. For purposes of this specification, the basic buffer shall include potassium or sodium carbonate. For purposes of this specification, the oxidant shall include potassium osmiumate and the co-oxidant shall include potassium ferrocyanide or iodine. Generally, the reaction is carried out in an aqueous $C_{1-6}$ alkanol such as t-butanol, isopropanol, methanol, or propanol in water, preferably t-butanol in water.

The molar ratio of formula 3 to ligand is typically 1:0.02–0.1. The molar ratio of formula 3 to oxidant is typically 1:1.5 or greater. [As appreciated by those of skill in the art, "or greater" as used above shall indicate that the second named item, such as oxidant, in the above case may be used in an amount in excess of the named amount. That is, in the above case the molar ratio of formula 3 to oxidant may be, for example 1:2 or 1:3.] The molar ratio of formula 3 to co-oxidant is typically 1:1.5 or greater. The basic buffer shall be used in an amount to maintain the pH of the reaction at pH 7 to 14, preferably 7 to 10.

The reaction is allowed to proceed at 0 to 25° C. until substantially complete in 0.5 to 5 hours;

(b) oxidizing a compound of formula 9

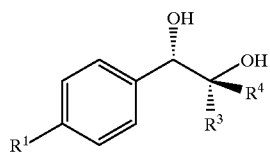

wherein $R^1$, $R^3$ and $R^4$ are described above;
with an oxidizing agent and optionally a first base to yield a compound of formula 1

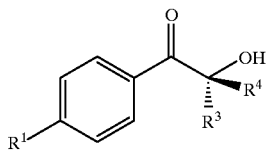

wherein $R^1$, $R^3$ and $R^4$ are described above;

The first base shall include alkylamines such as triethylamine, t-butylamine, isopropylamine and the like, preferably triethylamine. The oxidation conditions shall include those conditions known to convert an alcohol to a ketone such as the Swern oxidation, Des-Martin oxidation and the like.

The reaction is generally carried out in a non-reactive solvent such as benzene, toluene and xylene; etheral solvents such as diethyl ether, di-n-butyl and diisopentyl ethers, anisole, cyclic ethers such as tetrahydropyran, 4-methyl-1,3-dioxane, dihydropyran, tetrahydrofurfyl, methyl ether, ethyl ether, 2-ethoxytetrahydrofuran and tetrahydrofuran (THF); ester solvents including ethyl and isopropyl acetate; halo carbon solvents including mono or dihalo $C_{1-4}$ alkyl such as dichloromethane; $C_{6-10}$ linear, branched or cyclic hydrocarbon solvents including hexane; and nitrogen containing solvents including N,N-dimethylacetamide, N,N-dimethylformamide (DMF), N-ethylpyrrolidinone, N-methylpyrrolidinone, and acetonitrile. Preferable solvents are alcohol, dichloromethane, THF and DMF The molar ratio of formula 1 to first reagent is typically 1:4.0 or greater. The molar ratio of formula 1 to the second reagent is typically 1:2.0 or greater. The molar ratio of formula 1 to first base is typically 1:5 or greater.

The reaction is allowed to proceed at 0 to 25° C. until substantially complete in 0.5 to 5 hours.

(c) reacting a compound of formula 1

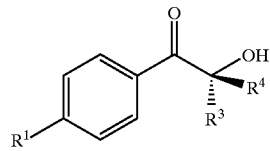

with a compound of the formula

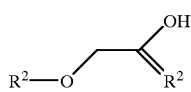

wherein $R^2$ is described above,
an activating agent, optionally a dehydrating agent, a suitable catalyst, and a second base to yield a compound of formula I

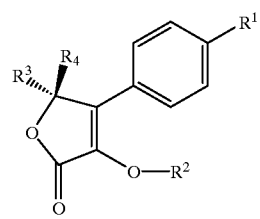

For purposes of this specification, the activating agent shall include CMC, 1,3-dicyclohexylcarbodiimide (DCC), 1-(3-dimethylaminopropyl)-3-ethylcarbodiimide (EDC),), 1-(3-dimethylaminopropyl)-3-ethylcarbodiimide hydrochloride (EDCl) and the like, preferably CMC. The dehydrating agent shall include isopropyltrifluoroacetate. The suitable catalyst shall include 4-Dimethylaminopyridine (DMAP), pyridine or other pyridine derivatives. The second base shall include 1,8-Diazabicyclo[5.4.0]undec-7-ene (DBU), 1,5-diazabicyclo[4.3.0]non-5-ene or an alkylamine such as triethylamine, t-butylamine, isopropylamine, and the like.

For purposes of this specification, the reaction is generally carried out in a non-reactive solvent such as benzene, toluene and xylene; etheral solvents such as diethyl ether, di-n-butyl and diisopentyl ethers, anisole, cyclic ethers such as tetrahydropyran, 4-methyl-1,3-dioxane, dihydropyran, tetrahydrofurfuryl, methyl ether, ethyl ether, 2-ethoxytetrahydrofuran and tetrahydrofuran (THF); ester solvents including ethyl and isopropyl acetate; halo carbon solvents including mono or dihalo $C_{1-4}$ alkyl such as dichloromethane; $C_{6-10}$ linear, branched or cyclic hydrocarbon solvents including hexane; and nitrogen containing solvents including N,N-dimethylacetamide, N,N-dimethylformamide (DMF), N-ethylpyrrolidinone, N-methylpyrrolidinone, and acetonitrile. Preferable solvents are alcohol, dichloromethane, THF and DMF.

The molar ratio of formula 1 to 2 is approximately 1:1. The molar ratio of formula 1 to second dehydrating agent is typically 1:1.3 or greater. The molar ratio of formula 1 to catalyst is typically 1:0.1 or greater.

The reaction is allowed to proceed at 0 to 25° C. until substantially complete in 0.5 to 5 hours.

In a second aspect, the invention encompasses a process for making a compound of formula 3

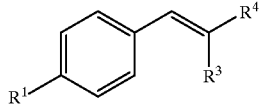
3 wherein $R^1$ is $SCH_3$ and $—S(O)_2CH_3$ and $R^3$ and $R^4$ are described above;
comprising
  (a) reacting a compound of formula 4

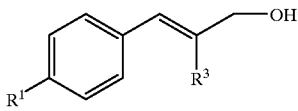
4 with a hindered base, and an anhydride or acid halide to yield a compound of formula 8.

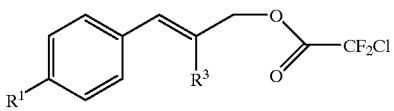
8

The hindered base shall include diisopropylethylamine, alkyl piperidine, alkyl pyridine and the like, preferably diisopropylethylamine. The anhydride or acid halide shall include chlorodifluoroacetic anhydride, acetic anhydride, acid chloride or bromide and the like, preferably chlorodifluoroacetic anhydride. The reaction carried out using a solvent such as N,N-di-methylformamide (DMF), dimethyl acetamide (DMAC), 1-ethyl-2-pyrrolidinone (NEP), 1-methyl-2-pyrrolidinone (NMP) and the like, preferably DMF.

The molar ratio of formula 4 to anhydride or acid halide is typically 1:1 to 1:1.4. The molar ratio of formula 4 to hindered base is typically 1:2 to 1:2.5.

The reaction is allowed to proceed at 0 to 25° C. until substantially complete in 0.5 to 5 hours.

(b) reacting without purification the compound of formula 8

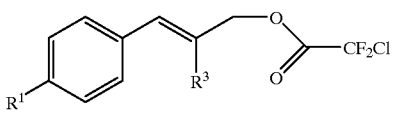
8 with a fluoride salt and metal halide, to yield a compound of formula 3.

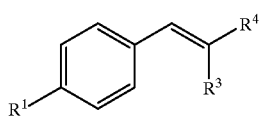
3

For purposes of this specification the fluoride salt shall include sodium, potassium or lithium fluoride and the metal halide shall include cuprous iodide.

The molar ratio of formula 8 to fluoride salt is typically 1:1 to 1:1.4. The molar ratio of compound of formula 8 to metal halide is typically 1:1 to 1:1.5.

The reaction is allowed to proceed at 0 to 25° C. until substantially complete in 0.5 to 5 hours.

In a third aspect, the invention encompasses a process of making a compound of formula 3

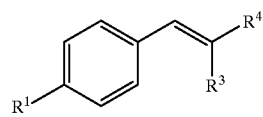
3 wherein:
  $R^1$ is selected from the group consisting of $—S(O)_2CH_3$ and $—SCH_3$;
  $R^3$ is H, $C_{1-4}$alkyl optionally substituted with 1 to 3 groups of F, Cl or Br and
  $R^4$ is H, $C_{1-4}$alkyl optionally substituted with 1 to 3 groups of F, Cl or Br, with the proviso that $R^3$ and $R^4$ are not the same,
comprising
  (a) reacting a compound of formula 4

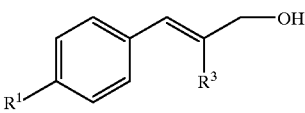
4 with imidazole and a halide in the presence of triphenylphosphine to yield a compound of formula 7.

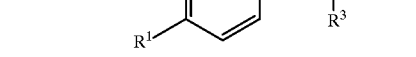
7

(b) reacting the compound of formula 7 with an alkyl cuprate to yield a compound of formula 3.

In a fourth aspect, the invention encompasses a process of making a compound formula 4

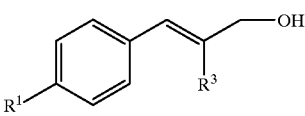
4 wherein $R^1$ is $SCH_3$ and $—S(O)_2CH_3$ and $R^3$ is described above,
comprising
  (a) reacting a compound of formula 5

5 wherein $R^{1a}$ is $NH_2SO_2$, $—S(O)_2CH_3$ or $CH_3S$ with triethyl 2-phosphonopropionate,

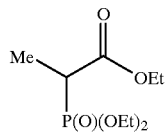

and a suitable Lewis acid, in an amine base, to yield a compound of formula 6a

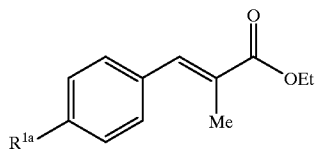

For purposes of this specification, the amine base includes, but is not limited to triethylamine, t-butylamine, isopropyl amine and the like, preferably triethylamine. For purposes of this specification the Lewis acid includes magnesium halide, wherein halide is bromo, chloro and iodo and the like, preferably magnesium bromide.

The reaction is generally carried out using a solvent such as benzene, toluene and xylene; etheral solvents such as diethyl ether, di-n-butyl and diisopentyl ethers, anisole, cyclic ethers such as tetrahydropyran, 4-methyl-1,3-dioxane, dihydropyran, tetrahydrofurfuryl, methyl ether, ethyl ether, 2-ethoxytetrahydrofuran and tetrahydrofuran (THF); ester solvents including ethyl and isopropyl acetate; halo carbon solvents including mono or dihalo $C_{1-4}$ alkyl such as dichloromethane; $C_{6-10}$ linear, branched or cyclic hydrocarbon solvents including hexane; and nitrogen containing solvents including N,N-dimethylacetamide, N,N-dimethylformamide (DMF), N-ethylpyrrolidinone, N-methylpyrrolidinone, and acetonitrile. Preferable solvents are alcohol, dichloromethane, THF and DMF.

The molar ratio of compound of formula 5 to propionate is typically 1:1 or greater. The molar ratio of compound of formula 5 to the amine base is 1:1 or greater. The molar ratio of compound of formula 5 to Lewis acid is 1:1 or greater;

The reaction is allowed to proceed at 0 to 25° C. until substantially complete in 0.5 to 5 hours;

(b) reacting a compound of formula

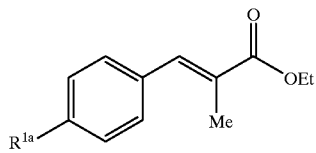

in an $C_{1-6}$ alkanol solvent and under acidic conditions, with a suitable catalyst and an oxidizing agent to yield a compound of formula 6b

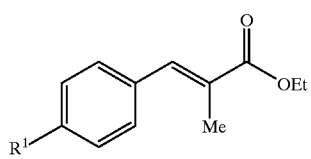

For purposes of this specification, the $C_{1-6}$ alkanol may include methanol, ethanol, propanol, isopropanol, pentanol and the like. For purposes of this specification, the catalyst includes sodium tungstate. The acidic conditions may be maintained by addition of an acid such as sulfuric acid, hydrochloric acid, fumaric acid and the like. For purposes of this specification the oxidizing agent includes hydrogen peroxide, t-butyl hydroperoxide or any oxidizing agent known in the art that will convert sulfide to sulfone.

The molar ratio of compound of formula 6a to oxidixing agent is typically 1:1 or greater. The molar ratio of compound of formula 6a to catalyst is typically 1:0.01 or greater. The molar ratio of compound of formula 6a to acid is typically 1:0.01 or greater.

The reaction is allowed to proceed at 0 to 25° C. until substantially complete in 0.5 to 5 hours.

(c) reacting a compound of formula 6b

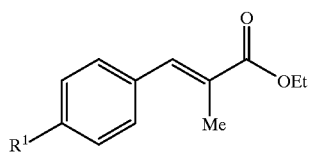

with a suitable reducing agent to yield a compound of formula 4

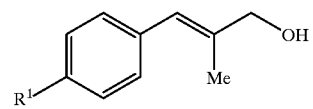

For purposes of this specification, the reducing agent includes, but is not limited to diisobutylaluminium hydride, lithium aluminum hydride, diisopropyl aluminum hydride, or any known agent that will reduce an ester to an alcohol.

The reaction is generally carried out using a non-reactive solvent such as benzene, toluene and xylene; etheral solvents such as diethyl ether, di-n-butyl and diisopentyl ethers, anisole, cyclic ethers such as tetrahydropyran, 4-methyl-1,3-dioxane, dihydropyran, tetrahydrofurfuryl, methyl ether, ethyl ether, 2-ethoxytetrahydrofuran and tetrahydrofuran (THF); ester solvents including ethyl and isopropyl acetate; halo carbon solvents including mono or dihalo $C_{1-4}$ alkyl such as dichloromethane; $C_{6-10}$ linear, branched or cyclic hydrocarbon solvents including hexane; and nitrogen containing solvents including N,N-dimethylacetamide, N,N-dimethylformamide (DMF), N-ethylpyrrolidinone, N-methylpyrrolidinone, and acetonitrile. Preferable solvents are alcohol, methylene chloride, THF and DMF.

The molar ratio of compound of formula 6b to reducing agent is 1:1 to 1:2.5 or greater.

The reaction is allowed to proceed at 0 to 25° C. until substantially complete in 0.5 to 5 hours.

Throughout the instant application, the following abbreviations are used with the following meanings:

| | |
|---|---|
| CMC = | 1-cyclohexyl-3-(2-morpholino-ethyl)carbodiimide metho-p-toluenesulfonate |
| COX = | cyclooxygenase |
| DBU = | 1,8-Diazabicyclo [5.4.0] undec-7-ene |
| DCC = | 1,3-dicyclohexylcarbodiimide |
| (DHQD)$_2$AQN = | 1,4-bis(dihydroquinidinyl)anthraquinone |
| (DHQD)-CLB = | hydroquinidine 4-chlorobenzoate |
| (DHQD)$_2$DPP = | hydroquinidine 7,8-diphenyl-1,4-pyrazinopyridazinediyldiether |
| (DHQD)$_2$-DP-PHAL = | hydroquinidine 7,8-diphenyl-1,4-phthalazinediyldiether |
| (DHQD)$_2$PHAL = | hydroquinidine 1,4-phthalazinediyl diether |
| (DHQD)-PHN | hydroquinidine 9-phenanthoyl ether |
| (DHQD)$_2$PYR = | hydroquinidine 2,5-diphenyl-4,6-pyrimidinediyl diether |
| DMAP = | 4-Dimethylaminopyridine |
| DMF = | N,N-dimethylformamide |
| ECC = | 1-(3-dimethylaminopropyl)-3-ethylcarbodiimide |
| EDCl = | 1-(3-dimethylaminopropyl)-3-ethylcarbodiimide hydrochloride |
| mCPBA = | meta-chloroperbenzoic acid |
| MMPP = | magnesium monoperoxyphthalate |
| NSAID = | non-steroidal anti-inflammatory drug |
| r.t. = | room temperature |
| THF = | tetrahydrofuran |

The invention will now be illustrated by the following non-limiting examples in which, unless stated otherwise:

(i) all operations were carried out at room or ambient temperature, that is, at a temperature in the range 18–25° C.;

(ii) evaporation of solvent was carried out using a rotary evaporator under reduced pressure (600–4000 pascals: 4.5–30 mm Hg) with a bath temperature of up to 60° C.;

(iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), M.P. (melting point), L (liter (s)), mL (milliliters), g (gram(s)), mg (milligrams(s)), mol (moles), mmol (millimoles), equiv (equivalent(s)).

EXAMPLE 1

Step 1: (2E) Ethyl 2-methyl-3-(4-methylthiophenyl)propenate (Compound 6a)

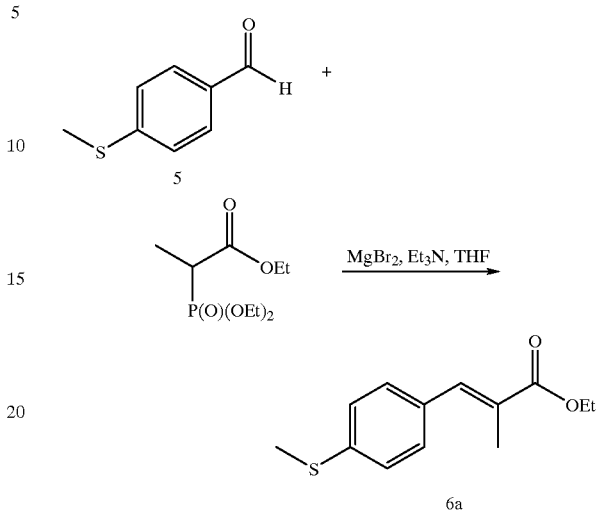

To a solution of triethyl 2-phosphonopropionate (47 g, 0.19 mol) in THF (200 mL) was added solid magnesium bromide etherate (59 g, 0.23 mol) under nitrogen. Triethylamine (26.5 mL, 0.19 mol) was added after 5 min. The mixture was stirred for 10 min and 4-(methylthio)benzaldehyde (27.1 mL, 0.19 mol) was added. After 15 h at room temperature the mixture was diluted with water (400 mL) and hexane (400 mL). The two layers were separated. The organic layer was washed with water (400 mL), dried over 4 Å molecular sieves, filtered, and concentrated to give 42.5 g (95%) of ester 6a as a light yellow oil: IR (neat) 2980, 1705, and 1240 cm$^{-1}$; $^1$H NMR (CDCl$_3$, 300 MHz) δ 7.63 (1 H), 7.33 (2 H), 7.25 (2 H), 4.26 (2 H), 2.50 (3 H), 2.12 (3 H), and 1.34 (3 H); $^{13}$C NMR (CDCl$_3$, 75.5 MHz) δ 168.71, 139.37, 138.08, 132.55, 130.19, 127.98, 125.89, 60.87, 15.38, 14.37 and 14.17.

Step 2: (2E) Ethyl 2-methyl-3-(4-methylsulphonylphenyl)propenate (Compound 6b)

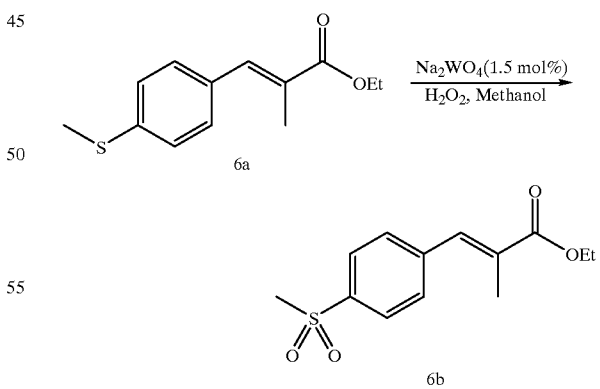

To a solution of sulfide 6a (2.36 g, 10 mmol), Na$_2$WO$_4$·2 H$_2$O (49.5 mg, 0.15 mmol), and H$_2$SO$_4$ (1 M, 68 μL) in methanol (10 mL) was added dropwise 30% H$_2$O$_2$ (2.6 mL) at room temperature under nitrogen maintaining the temperature at 38–45° C. The mixture was aged at ambient temperature for 3 h and cooled ~18° C. Sodium sulfite (20% aqueous solution, 2.6 mL) was added slowly with an external cooling to maintain the temperature below 20° C. After aged for 0.5 h the mixture was diluted with water (20 mL) and filtered. The solid was washed with water (2×10 mL) and dried in vacuo to give 2.55 g of 6b as a light yellow solid: IR (thin film) 1700 cm$^{-1}$; $^{1}$H NMR (CDCl$_3$, 300 MHz) δ 7.92 (2 H), 7.64 (1 H), 7.52 (2 H), 4.24 (2 H), 3.04 (3 H), 2.05 (3 H), and 1.30 (3 H); $^{13}$C NMR (CDCl$_3$, 75.5 MHz) δ 167.88, 141.50, 139.76, 136.29, 131.87, 130.21, 127.45, 61.24, 44.45, 14.28, and 14.14.

Step 3: (2 E) 2-methyl-3-(4-methylsulphonylphenyl) propanol (Compound 4b)

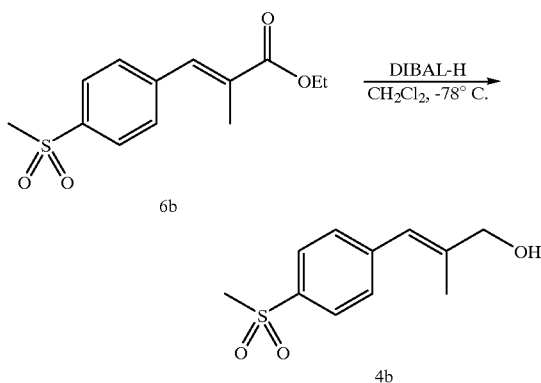

To a solution of ester 6b (34.8 g, 0.13 mol) in dichloromethane (200 mL) was added neat DIBAL-H (57.8 mL, 0.33 mol) dropwise at −78° C. under nitrogen. The reaction mixture was stirred at −78° C. for an additional 1 h. and quenched cautiously with methanol (25 mL). Saturated NH$_4$Cl solution (500 mL) was added slowly after the mixture was warmed to 0° C. The mixture was aged at ambient temperature for 1 h and filtered. The solid was washed with dichloromethane (2×300 mL). The filtrate and washes were combined and the two layers were separated. The aqueous layer was extracted with dichloromethane (150 mL). The combined organic solutions were dried over 4 Å molecular sieves, filtered, and concentrated to give 29.2 g (99%) of 4b as a white solid: IR (thin film) 3480 and 1600 cm$^{-1}$; $^{1}$H NMR (CDCl$_3$, 300 MHz) δ 7.84 (2 H), 7.38 (2 H), 6.55 (1 H), 4.19 (2 H), 3.05 (3 H), 2.34 (1 H), and 1.86 (3 H); $^{13}$C NMR (CDCl$_3$, 75.5 MHz) δ 143.58, 141.53, 137.79, 129.60, 127.24, 122.51, 68.02, 44.58, and 15.42.

Step 4: (E) 1-(4-methylsulphonylphenyl)-2-methyl-4,4,4-trifluorobutene Compound (3b)

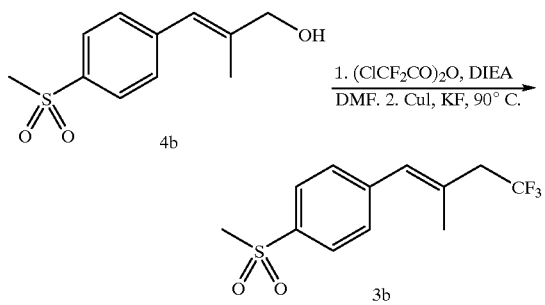

To a solution of alcohol 4b (11.30 g, 50 mmol) and diisopropylethylamine (21 mL, 0.12 mol) in DMF (50 mL) was added dropwise chlorodifluoroacetic anhydride (11 mL, 60 mmol) under nitrogen with an external cooling bath to maintain the temperature at 20–30° C. Potassium fluoride (3.5 g, 60 mmol) and cuprous iodide (9.5 g, 50 mmol) were added after 5 min. The mixture was heated at 90° C. for 1 h, poured into 100 g of ice, extracted with ethyl acetate (2×100 mL), and concentrated. The residue was transferred into a funnel containing ~250 g of silica gel and eluted with 15% ethyl acetate in hexane. Concentration of the eluent gave 10.3 g (74%) of 3b as a white solid: IR (thin film) 1600 and 1352 cm$^{-1}$; $^{1}$H NMR (CDCl$_3$, 300 MHz) δ 7.88 (2 H), 7.40 (2 H), 6.48 (1 H), 3.04 (3 H), 2.94 (2 H), and 1.94 (3 H); $^{13}$C NMR (CDCl$_3$, 75.5 MHz) δ 142.63, 138.66, 131.39, 130.52, 129.73, 127.80, 127.33, 124.12, 44.35 (q), 43.97, 43.59, and 18.50.

Step 5: (2E) 2-methyl-3-(4-methylthiophenyl)propanol Compound (4a)

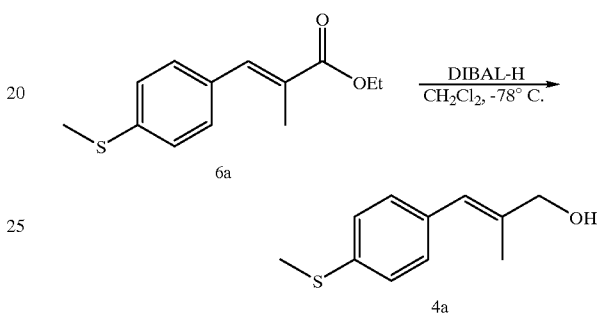

To a solution of ester 6a (11.8 g, 50 mmol) in dichloromethane (200 mL) was added neat DIBAL-H (22.3 mL, 0.125 mol) dropwise at −78° C. under nitrogen. The reaction mixture was stirred at −78° C. for an additional 1 h. and quenched cautiously with methanol (25 mL). Saturated NH$_4$Cl solution (200 mL) was added slowly after the mixture was warmed to −40° C. The mixture was aged at ambient temperature for 1 h and the two layers (with some aluminum solid) were separated. The aqueous layer was extracted with dichloromethane (2×100 mL). The combined organic solutions were dried over 4 Å molecular sieves, filtered, and concentrated to give 9.7 g (100%) of 4a as a white solid: mp. 76–77° C. IR (thin film) 3500 and 1495 cm$^{-1}$; $^{1}$H NMR (CDCl$_3$, 300 MHz) δ 7.20 (4 H), 6.46 (1 H), 4.17 (2 H), 2.49 (3 H), 1.94 (1 H), and 1.89 (3 H); $^{13}$C NMR (CDCl$_3$, 75.5 MHz) δ 137.52, 136.40, 134.50, 129.37, 126.38, 124.43, 69.00, 15.90, and 15.42.

Step 6: (E) 1-(4-methylthiophenyl)-2-methyl-4,4,4-trifluorobutene Compound (3a)

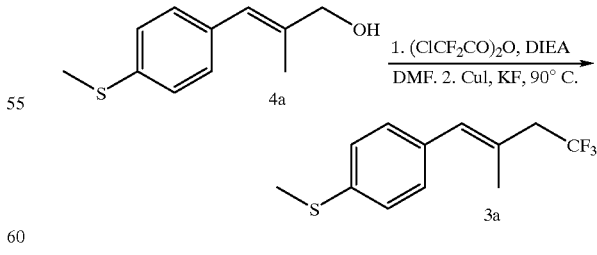

To a solution of alcohol 4a (9.5 g, 48.9 mmol) and diisopropylethylamine (20.5 mL, 0.12 mol) in DMF (100 mL) was added dropwise chlorodifluoroacetic anhydride (10.8 mL, 58.7 mmol) under nitrogen with an external cooling bath to maintain the temperature at 0–10° C. Potassium fluoride (3.5 g, 60 mmol) and cuprous iodide (9.5 g, 50 mmol) were added after warm up to room temperature. The mixture was heated at 90° C. for 1 h, cooled to room temperature, quenched with ice (100 g), and filtered through a pad of solkafloc. The cake was washed with ethyl acetate (3×100 mL). The filtrate and washes were combined and the two layers were separated. The organic layer was washed with saturated NH$_4$Cl (2×50 mL) and concentrated, The residue was transferred to ~50 g of silica gel and the product was eluted with hexane. Concentration of the eluent gave 7.3 g (61%) of 3a as a light yellow oil: IR (neat) 1600 cm$^{-1}$; $^1$H NMR (CDCl$_3$, 300 MHz) δ 7.24 (4 H), 6.43 (1 H), 2.93 (2 H), 2.51 (3 H), and 1.99 (3 H); $^{13}$C NMR (CDCl$_3$, 75.5 MHz) δ 137.17, 133.90, 131.67, 129.43, 127.59, 126.24, 44.64, 44.30 (q), 18.45, and 15.73.

Step 7: Diol Compound 9b

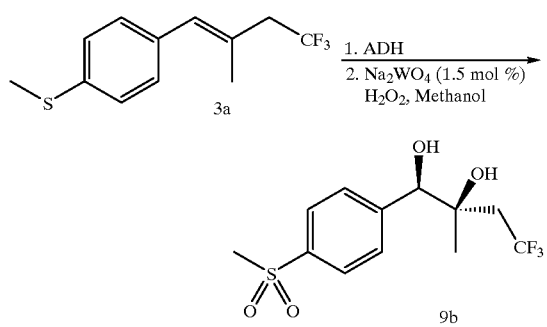

(DHQD)$_2$PHAL (1.44 g, 1.76 mmol) and potassium osmate dihydrate (129 mg, 0.35 mmol) were dissolved in a mixture of water (175 mL) and tert-butyl alcohol (175 mL) under nitrogen. After the mixture was stirred at ambient temperature for 1 h potassium carbonate (14.5 g, 105 mmol) and potassium ferricyanide(III) (34.6 g, 105 mmol) were added. The temperature of the mixture was adjusted to 18–20° C. and 3a (8.62 g, 35 mmol) was added. After 15 h the reaction was quenched with sodium sulfite (15 g) in water (100 mL) and extracted with ethyl acetate (200 mL). The ethyl acetate solution was washed with brine (100 mL) and concentrated. The residue was dissolved in methanol (35 mL). Sulfuric acid (1 M, 0.24 mL) and sodium tungstate dihydrate (173 mg, 0.52 mmol) were added followed by slow addition of hydrogen peroxide (30% in water, 7.3 mL), maintaining the temperature at 45–50° C. After 3 h the mixture was diluted with water (100 mL) and extracted with ethyl acetate (3×100 mL). The combined extracts were washed with water (100 mL) and concentrated to dryness to give 10.5 g of the crude Diol 9b as a light yellow solid. SFC assay at this point indicated that the compound was 82% ee. The crude product was dissolved in hot IPAc (90 mL) and then cooled to 23° C. The crystal (1.5 g, 12% ee, 14.3% recovery) was collected by filtration. The filtrate was diluted with hexane (final ratio of IPAc/hexane: 4/5) and the crystal was collected by filtration to give 7.6 g of pure 9b (>98% ee, 72.4% recovery) as a white solid: mp. 140.5–142.5° C. IR (thin film) 3480 and 1380 cm$^{-1}$; $^1$H NMR (CDCl$_3$ and CD$_4$OD, 300 MHz) δ 7.73 (2 H), 7.49 (2 H), 4.44 (1 H), 3.86 (2 H), 2.95 (3 H), 2.30 (2 H), and 1.06 (3 H); $^{13}$C NMR (CDCl$_3$, 75.5 MHz) δ 146.90, 139.25, 129.00, 128.12, 126.57, 124.43, 78.06, 71.97, 44.14, 40.70 (q), and 22.35.

Step 7 Alternative: Diol Compound 9b from Compound 3b

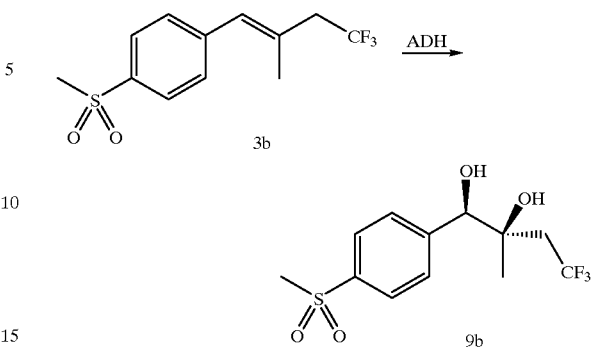

(DHQD)$_2$PHAL (0.82 g, 1 mmol) and potassium osmate dihydrate (73.7 mg, 0.20 mmol) were dissolved in a mixture of water (100 mL) and tert-butyl alcohol (100 mL) under nitrogen. After the mixture was stirred at ambient temperature for 1 h potassium carbonate (8.3 g, 60 mmol) and potassium ferricyanide(III) (19.8 g, 60 mmol) were added. The temperature of the mixture was adjusted to 18–20° C. and 3b (5.74 g, 20 mmol) was added. After 7 h the reaction was quenched with sodium sulfite (15 g) in water (100 mL) and extracted with ethyl acetate (2×100 mL). The ethyl acetate solution was washed with brine (100 mL) and concentrated to dryness to give 7.0 g of crude 9b (81.4% ee) as a light yellow solid. The product was purified as described previously and had exactly the same set of analytical properties as that obtained from 3a.

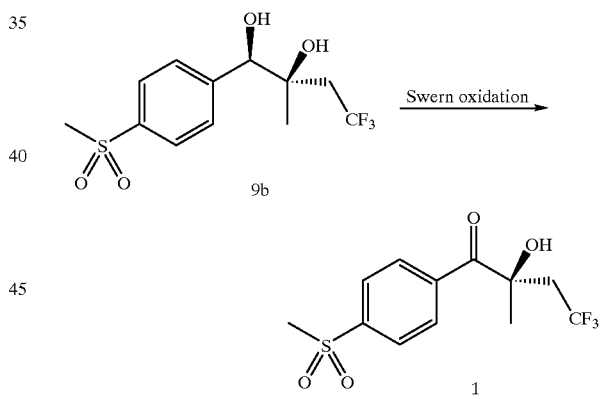

Step 8: α-Hydroxyl ketone Compound 1

To a solution of oxalyl chloride (0.36 mL, 4.2 mmol) in THF (5 mL) was added anhydrous dimethyl sulfoxide (0.60 mL, 8.4 mmol) at −78° C. After 20 min a solution of 9b (0.62 g, 2.0 mmol) in THF (2.5 mL) was added over 20 min. The mixture was quenched with triethylamine (2.5 mL, 18 mmol) after 2 h and allowed to warm to room temperature over 1 h. Water (10 mL) was added. The mixture was extracted with ethyl acetate (2×10 mL) and concentrated. The residue was recrystallized from toluene (3 mL) to give 0.58 g of 1 as a white solid: mp. 101.5–102.5° C. IR (thin film) 3510 and 1690 cm$^{-1}$; $^1$H NMR (CDC$_3$, 300 MHz) δ 8.17 (2 H), 7.98 (2 H), 3.04 (3 H), 2.96 (1 H), 2.72 (1 H), and 1.67 (3 H); $^{13}$C NMR (CDCl$_3$, 75.5 MHz) δ 201.81, 143.74, 138.95, 130.55, 127.44, 77.28, 44.29, 43.34, 43.20 (q), and 27.66.

Step 9: Compound 12

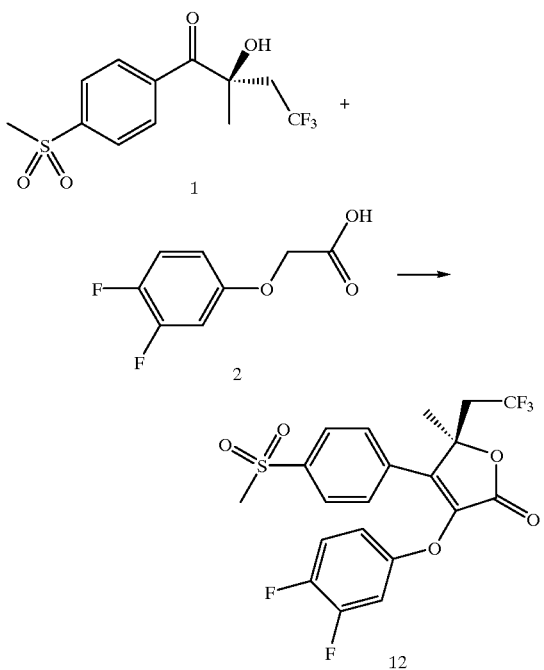

To a solution of 1 (0.23 g, 0.74 mmol) and 2 (0.17 g, 0.90 mmol) in methylene chloride (5 mL) was added CMC (0.49 g, 1.1 mmol). Isopropyl trifluoroacetate (0.13 mL, 0.89 mmol) and DBU (0.14 mL, 0.88 mmol) were then added after 1 h. The mixture was stirred at room temperature for 3 h and quenched with water (10 mL). The two layers were separated. The aqueous layer was extracted with methylene chloride (5 mL). The combined organic solutions were washed with 2 N NaOH (10 mL and water (10 mL), dried over 4 Å molecular sieves, decanted, and concentrated to give 0.36 g solid (91 A%) pure. The solid was further purified by recrystallization from absolute ethanol (3 mL): mp. 140–141° C. IR (thin film) 1775 and 1508 cm$^{-1}$; $^1$H NMR (CDCl$_3$, 300 MHz) δ 8.02 (2 H), 7.77 (2 H), 7.09 (1 H), 6.85 (1 H), 6.71 (1 H), 3.08 (3 H), 3.01 (1 H), 2.85 (1 H), and 1.84 (3 H); $^{13}$C NMR (CDCl$_3$, 75.5 MHz) δ 163.83, 145.85, 143.61, 142.01, 133.48, 129.08, 128.23, 122.63, 117.93, 117.90, 117.67, 112.72, 112.76, 112.66, 112.63, 112.58, 107.45, 107.17, 81.45, 44.32, 41.50 (q), and 26.67.

What is claimed is:

1. A process for making compounds of formula I

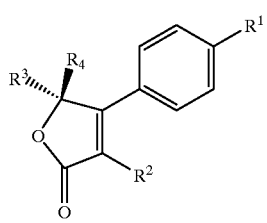

or a pharmaceutical salt thereof wherein
R$^1$ is selected from the group consisting of SCH$_3$, —S(O)$_2$CH$_3$ and —S(O)$_2$NH$_2$;
R$^2$ is selected from the group consisting of OR, mono or di-substituted phenyl wherein the substituents are selected from the group consisting of methyl, chloro and F;
R is unsubstituted or mono or di-substituted phenyl wherein the substituents are selected from the group consisting of methyl, chloro and F;
R$^3$ is H, C$_{1-4}$alkyl optionally substituted with 1 to 3 groups of F, Cl or Br and
R$^4$ is H, C$_{1-4}$alkyl optionally substituted with 1 to 3 groups of F, Cl or Br, with the proviso that R$^3$ and R$^4$ are not the same, the process comprising the steps of
(a) reacting a compound of formula 3

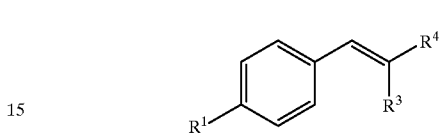

wherein R$^1$, R$^3$ and R$^4$ are described above;
with a first ligand, a basic buffer, an oxidant and optionally a co-oxidant to yield a compound of formula 9

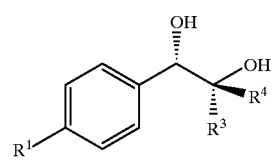

(b) oxidizing a compound of formula 9 with an oxidizing agent optionally in the presence of a first base to yield a compound of formula 1

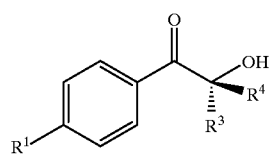

wherein R$^1$, R$^3$ and R$^4$ are described above; and
(c) reacting a compound of formula 1 with a compound of the formula 2

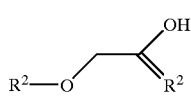

wherein R$^2$ is defined above,
an acylating agent, optionally a dehydrating agent, a suitable catalyst, and a second base to yield a compound of formula I.

2. A process according to claim 1 wherein the first ligand belongs to the group consisting of (DHQD)$_2$PHAL, (DHQD)$_2$DP-PHAL, (DHQD)$_2$PYR, (DHQD)-PHN, (DHQD)$_2$AQN, (DHQD)$_2$DPP and (DHQD)-CLB, the basic buffer belongs to the group consisting of potassium or sodium carbonate, the oxidant is potassium osmiumate and the co-oxidant belonging to the group consisting of potassium ferrocyanide and iodine.

3. A process according to claim 2 wherein the first ligand is (HDQD)$_2$PHAL.

4. A process according to claim 1 wherein the first base belongs to the group consisting of triethylamine, t-butylamine, and isopropylamine, the oxidizing agent is a complex of a first reagent belonging to the group consisting of dimethylsulfoxide, pyridinium chlorochromate, pyridinium dichromate, pyridinium fluorochromate and pyridinium fluorochromate and a second reagent belonging to the group consisting of oxalyl chloride, chlorine, and acetyl chloride.

5. A process according to claim 4 wherein the first base is triethylamine and the oxidizing agent is dimethylsulfoxide/oxalyl chloride.

6. A process according to claim 1 wherein the molar ratio of formula 9 to first reagent is 1:4.0 or greater and the molar ratio of formula 9 to second reagent is 1:2.0 or greater.

7. A process according to claim 1 wherein the acylating agent belongs to the group consisting of 1-cyclohexyl-3-(2-morpholino-ethyl)carbodiimide metho-p-toluenesulfonate, 1,3-dicyclohexylcarbodiimide, 1-(3-dimethylaminopropyl)-3-ethylcarbodiimide, and 1-(3-dimethylaminopropyl)-3-ethylcarbodiimide hydrochloride, the dehydrating agent is isopropyltrifluoroacetate, the catalyst belongs to the group consisting of 4-dimethylaminopyridine and pyridine, and the second base belongs to the group consisting of 1,8-diazabicyclo[5.4.0]undec-7-ene (DBU), 1,5-diazabicyclo[4.3.0]non-5-ene, triethylamine, t-butylamine, and isopropylamine.

8. A process according to claim 1 wherein the molar ratio of formula 1 to 2 is 1:1 or greater.

9. A process for making a compound of formula 3

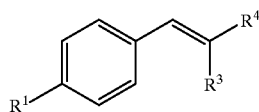

wherein:
R$^1$ is selected from the group consisting of —SCH$_3$ and —S(O)$_2$CH$_3$;
R$^3$ is H, C$_{1-4}$alkyl optionally substituted with 1 to 3 groups of F, Cl or Br and
R$^4$ is H, C$_{1-4}$alkyl optionally substituted with 1 to 3 groups of F, Cl or Br, with the proviso that R$^3$ and R$^4$ are not the same, comprising
(a) reacting a compound of formula 4

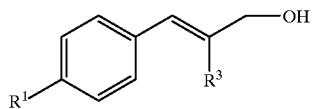

with a hindered base, and an ahydride or acid halide to yield a compound of formula 8.

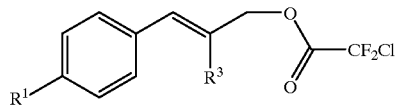

(b) reacting without purification the compound of formula 8 with a fluoride salt and metal halide, to yield a compound of formula 3.

10. A process according to claim 9 wherein the hindered base belongs to the group consisting of diisopropylethylamine, C$_{1-10}$ alkyl piperidine and C$_{1-10}$ alkyl pyridine and the ahydride or acid halide belongs to the group consisting of chlorodifluoroacetic anhydride, acetic anhydride, acid chloride and acid bromide.

11. A process according to claim 10 wherein the hindered base is diisopropylethylamine and the hydride is chlorodifluoroacetic anhydride.

12. A process according to claim 9 wherein the fluoride salt belongs to the group consisting of sodium, potassium or lithium fluoride and the metal halide is cuprous iodide.

13. A process according to claim 12 wherein the molar ratio of compound of formula 8 to metal halide is typically 1:1 to 1:1.5.

14. A process for making a compound of formula 3

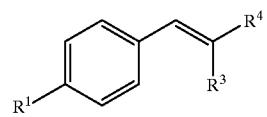

wherein:
R$^1$ is selected from the group consisting of —S(O)$_2$CH$_3$ and —SCH$_3$;
R$^3$ is H, C$_{1-4}$alkyl optionally substituted with 1 to 3 groups of F, Cl or Br and
R$^4$ is H, C$_{1-4}$alkyl optionally substituted with 1 to 3 groups of F, Cl or Br, with the proviso that R$^3$ and R$^4$ are not the same, comprising
(a) reacting a compound of formula 4

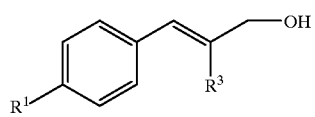

with imidazole and a halide in the presence of triphenylphosphine to yield a compound of formula 7.

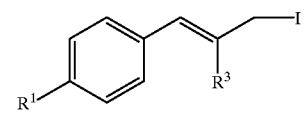

(b) reacting the compound of formula 7 with an alkyl cuprate to yield a compound of formula 3.

* * * * *